United States Patent [19]

Van Gemen et al.

[11] Patent Number: 5,679,553
[45] Date of Patent: Oct. 21, 1997

[54] PROCESS FOR RENDERING A NUCLEIC ACID AMPLICATION REACTION PRODUCT INCAPABLE OF BEING A TARGET FOR FURTHER AMPLIFICATION, A DIAGNOSTIC ASSAY EMPLOYING SAID PROCESS

[75] Inventors: Bob Van Gemen, Boxtel; Adriana Frederieke Schukkink, Houten, both of Netherlands

[73] Assignee: Akzo Nobel N.V., Arnhem, Netherlands

[21] Appl. No.: 519,478

[22] Filed: Aug. 25, 1995

[30] Foreign Application Priority Data

Aug. 25, 1994 [EP] European Pat. Off. ............. 94202438

[51] Int. Cl.$^6$ .............................. C12P 19/34; C12Q 1/68; C07H 21/04
[52] U.S. Cl. .............. 435/91.2; 435/6; 536/24.3
[58] Field of Search ................ 435/6, 91.2; 536/24.3

[56] References Cited

U.S. PATENT DOCUMENTS 5,273,890 12/1993 Steinman ........................ 435/91.2

FOREIGN PATENT DOCUMENTS

| 0370694 | 5/1990 | European Pat. Off. . |
|---|---|---|
| A 0552931 | 7/1993 | European Pat. Off. . |
| WO 91/12342 | 8/1991 | WIPO . |
| WO 91/17270 | 11/1991 | WIPO . |
| WO 93/05184 | 3/1993 | WIPO . |
| WO 93/25706 | 12/1993 | WIPO . |
| WO 94/24311 | 10/1994 | WIPO . |

OTHER PUBLICATIONS

J. Versailles et al., *PCR Methods and Applications*, 3:3:151–158, Dec. 1993.

Ullu et al, "2'–O–methyl RNA oligonucleotides identify two functional elements in the trypanosome spliced leader ribonucleoprotein particle", J. Biol. Chem. 268(18):13068–13073 Jun. 1993.

Wasserman et al, "Structural analyses of the 7SK ribonucleoprotein (RNP), the most abundant human small RNP of unknown function", Mol. Cell. Biol. 11(7):3432–3445 Jul. 1991.

Stratagene catalog, p. 39 1988.

Yap et al, "False positives and contamination in PCR", in PCR Technology: Current Innovations, CRC Press, Boca Raton, Fl pp. 249–258 1994.

DeFilippes, "Decontaminating the polymerase chain reaction", Biotechniques 10(1):26, 28, 30 1991.

Zhu et al, "The use of exonuclease III for polymerase chain reaction sterilization", Nucleic Acids Res. 19(9): 2511 1991.

Hod, "A simplified ribonuclease protection assay", Biotechniques 13(6):852–853 1992.

Saccomanno et al, "A faster ribonuclease protection assay", Biotechniques 13(6):847–849 1992.

Yang et al, "Application of the polymerase chain reaction to the ribonuclease protection assay", Biotechniques 13(6):922–927 1992.

*Primary Examiner*—W. Gary Jones
*Assistant Examiner*—Jeffrey Fredman
*Attorney, Agent, or Firm*—Mary E. Gormley

[57] ABSTRACT

A process for making the product of a nucleic acid amplification reaction, which amplification reaction employs one or more primer pairs, incapable of being a target for further amplification comprising: contacting the amplified product with an oligonucleotide capable of hybridizing to a stretch a nucleotides of the amplified product, said stretch being situated between the hybridisation sites of a pair of primers, under conditions which allow formation of a hybridisation complex between the oligonucleotide and the amplified product to occur, said oligonucleotide being modified in such a way that it.protects the double stranded part of the hybridisation complex hybridized to the oligonucleotide from degradation, and subjecting the hybridisation complex to a degradative treatment under circumstances such that at least the part of the hybridisation complex capable of hybridizing to the primers is degraded.

An assay for diagnosing the presence of a nucleic acid sequence in a sample comprising carrying out the above-mentioned method and a kit for carrying out the above-mentioned method are also disclosed.

29 Claims, No Drawings

PROCESS FOR RENDERING A NUCLEIC ACID AMPLICATION REACTION PRODUCT INCAPABLE OF BEING A TARGET FOR FURTHER AMPLIFICATION, A DIAGNOSTIC ASSAY EMPLOYING SAID PROCESS

FIELD OF THE INVENTION

The subject invention lies in the field or biotechnology, in particular the field of amplification of nucleic acid.

BACKGROUND OF THE INVENTION

The greatest problem facing the diagnostic application of PCR and other nucleic acid amplification methods is false positivity due to contaminating nucleic acids (Kwok, S., and R. Higuehi. 1989. Awarding false positive with PCR. Nature (London) 339:237–238.) The exquisite sensitivity of PCR proves to be its undoing; the transfer of miniscule quantities of such sequences into a neighbouring container may result in a false positive result. Nucleic acid contamination may result from 3 sources. One source consists of clinical specimens containing large numbers of target molecules, resulting in cross-contamination between specimens. Another source is contamination of reagents used in PCR by previously cloned plasmid DNA. The third source is accumulation of PCR products (amplicons) in the laboratory by repeated amplification of the same target sequence. The latter is in particular of relevance in diagnostic applications.

Beside the potential contamination of PCR via spills and splashes of plasmids, restriction fragments of PCR products from previous amplification, there are other sources of carry-over. The barrel of pipetting devices may be contaminated with aerosols, which may lead to cross-contamination. DNA sticking on microtome blades as well as on razor blades may be carried over to a subsequent PCR. Also equipment used during preparation of samples or analysis of PCR products, for example gel apparatus, dotblot apparatus, centrifuges or dry ice/ethanol baths may be a potential source of contamination (S. Kwok (1989), Amplification 2, p. 4). Some general physical precautions which have dramatically reduced false negative rates are separation of laboratory areas where nucleic acid is isolated from samples, laboratory areas where amplification reactions are set up and laboratory areas where the actual amplification and detection take place. Further the use of separate sets of supplies and piperring devices dedicated for sample preparation and setting up reactions can also contribute to a reduction. These measures regarding laboratory organisations will however not completely prevent contamination of reactions following the amplification of nucleie acid material and are cumbersome and costly. While the precautions can be adopted by research laboratories they will represent severe limitations to service laboratories until prepackaged quality controlled diagnostic kits become available. Presently, clinical microbiology laboratories have neither the space to devote exclusively to PCR nor the inclination to trouble-shoot false positives frequently.

Amplicon contamination is the most serious kind of contamination and unfortunately the most likely to occur because of the large numbers of molecules that are generated in a standard reaction. Each amplification vessel may contain as many as $10^{12}$ copies of an amplicon, thus, even the tiniest aerosol droplet (10–6 µl) may contain up to $10^5$ potential targets. Amplicons are by definition proven of PCR substrates and are thus ideal targets for further amplification. When one considers the fact that hundreds to thousands of amplification reactions may be performed in the optimization and testing of a new set of reagents it is not surprising that amplicon buildup can manifest itself in the contamination of reagents, buffers, laboratory glassware, autoclaves and ventilation systems. This problem is especially acute in the diagnosis of infectious diseases, in which assays are generally tuned for maximum sensitivity (1 to 10 template molecules).

Besides the general laboratory precautions several physical methods have been developed to overcome contamination of amplification reactions with non-target DNA.

A number of patent applications have been filed which are directed at reduction of contamination of amplification reactions with previously amplified nucleic acid products. In WO 9117.270 a method is described for reducing amplification product contamination in an amplification procedure comprising production of a distinguishably modified amplification product using a modified amplification primer and contacting the modified amplification product (AP) with a means for selectively eliminating the modified AP. The modification is selected from ligands, crosslinking agents, or enzyme recognition sites. The preferred means of selectively eliminating the modified AP is use of an RNase enzyme site. This approach only works by incorporating an RNase site on a DNA primer, otherwise RNase will not work. This method can only be used for PCR or LCR but dannot be used in a NASBA (RNA amplification) reaction. Alternatively the means for eliminating modified AP is described as being an immobilised specific partner for the ligand especially biotin or fluorescein. In the described method the re-amplification is prevented however only after carry-over of the product has occurred. This means the detection reaction of the amplification product can still result in carry-over of the amplification product to a subsequent amplification reaction.

In WO 9201-814 sterilising a uucleic acid amplification reaction system contaminated with nucleic acid sequences from a previous amplification resulting from mixing conventional and unconventional nTP's comprising degrading the contaminating amplified product by hydrolysing covalent bonds of the unconventional nucleotides is disclosed.

In EP 496483 of Integrated DNA Technologies Inc. a process is described for reducing contamination by an amplified product in nucleic acid amplification reactions using a primer or polynucleotide substrate containing a ribose residue in the amplification reaction followed by cleaving the ribonucleotide linkage within the amplified product. The cleavage eliminating the amplification product and thereby preventing carry-over occurs after detection of the amplified product and potentially thereby after carry-over of amplified product has occurred. Subsequently prior to further amplification reactions cleavage of ribose should be carried out. The amplification reaction on which this method can be use may be PCR, LCR or transcription based reaction. It cannot be used for NASBA or any other amplification reaction that employs RNA.

In EP 522884 of Life Technologies Inc. a process of oligonucleotide dependent amplification of nucleic acid comprising amplification in a first sample, said amplification being dependent on one or more oligonucleotides comprising an exo-sample nucleotide at or near one or more of its termini to produce amplified nucleic acid and treating a second sample such that the amplified nucleic acid is rendered unamplifiable without preventing amplifications of nucleic acid not containing exonucleotide is described. Also disclosed is a method of detecting target nucleic acid in a sample by providing single stranded nucleic acid and 4 or more DNA probes followed by repeatedly performing the cycle of hybridising the probes, ligating to form probe sequences and denaturing DNA in the sample and detecting the joined probe sequences. The first and second probes are primary. They are single stranded and capable of hybdridising to parts of a strand or target nucleic acid such that the probes can be joined. The third and fourth probes hybdridise to the first and second probes respectively. At least the 3' nucleotide of the first and 5' nucleotide of the second probe are deoxyuridine as are the 3' nucleotide of the fourth probe of the 5' nucleotide of the 3rd probe. Before detecting the joined probe sequences the sample is treated with UDG so that glycosidic bonds between the uracil and deoxyribose moieties of joined probes are cut. In a variant on this method EP 401-037 discloses that the amplified nucleic acid also incorporates deoxyuridine so the amplified product as such cannot serve as template.

In WO 9200384 it is described that after stopping amplification cycles the amplification products are rendered incapable of further amplification and/or before start of PCR a pretreatment is applied which prevents selectively the reaction of amplification products formed earlier in a PCR reaction using the same primer. The primer can contain ribose residues and agents which cause a cut in the complementary sequences or else form a covalent bridge between the two chains of DNA bound by 2 primers such as psoralen. Psoralens will form interstrand cross-links after interpolation in double stranded DNA and photoactivation with light of wave length of 23-400 Nm. Another option is the use of gamma irradiation of genomic DNA in the presence of all PCR reagents accept Taq DNA-Polymerase. After irradiation the PCR mixture remains capable of amplifying freshly added target DNA but higher doses seem to reduce amplification efficiency. The inactivation is dependent on length and nature of the DNA template and has to be optimized for every individual amplification system.

The use and the possible drawbacks of UV irradiation to control contamination in PCR has also been discussed extensively. Beside non-dimer photodamage of DNA the major pathway of UV-inactivation is the crosslinking of adjacent pyrimidines on the same DNA strand. The reaction is photo-reversible and there will be a steady-state between dimerized and non-dimerized pyrimidine pairs. The fraction of dimerized pyrimidines represents the percent of observed UV-inactivation of a given DNA target.

Due to the reversibility of dimerization, both length and internal sequence of a DNA target must be taken into account. Longer sequences having a greater number of thymidine pairs are easier to inactivate than smaller ones. Adding Taq DNA polymerase and true target DNA after successful UV-irradiation may nevertheless produce a certain level of false positive PCR signals (BFE vol. 8 nr. 10, oktober 1991, Martin Heinrich, PCR carry-over).

The use of the psoralen derivative 4-aminoethyl-4,5'-dimethylisopsoralen (4'-AMDMIP) has been described (Cimino, G. D., K. C. Metchette, J. W. Tessman, J. E. Hearst, and S. T. Isaacs. 1991, Nucleic Acids Res. 19:99–107 and Isaacs, S. T. et al. 1991, Nucleic Acids Res. 19:109–116). This compound is added to the PCR mixture prior to amplification; it does not substantially interfere with primer annealing or Taq polymerase activity and is thermally stable. After amplification but before the polypropylene reaction tubes are opened, the tubes are exposed to long-wave UV light, which penetrates them and photochemically activates the isopsoralen but does not otherwise damage the DNA. the activated psoralen then formes cyclobutane adducts with pyrimidine residues on the amplified DNA that prevent Taq polymerase from traversing the molecule in a subsequent amplification. The efficiency of this process is dictated in part by probability and can be extremely high, depending on the length and nucleotide base composition of the amplicon. In general, for amplicons greater than 300 bp in length with roughly G + C content, virtually complete sterilization can be achieved. However, both sterilization methods using isopsoralen and using uridine have left room for improvement. In the photochemical procedure, inhibition of PCR has been observed at high isopsoralen concentrations, the sort of concentration that might be necessary to inacativate very short or highly GC-rich amplicons. In addition, when internal hybridisation probes are used for detection of the amplicons, lower hybridization stringencies may be required to compensate for the presence of isopsoralen cross-links in the amplified DNA. Potential problems with the UNG protocol include incomplete ablation of UNG activity at the elevated temperatures used for denaturation and annealing in the PCR procedure. Residual UNG activity may affect the sensitivity of the system because in the early cycles of PCR the uracil-containing strands may be inactivated as soon as they are made. In addition, the substitution of dUTP for ITP in many PCR protocols results in lower amplification efficiency, requiring adjustment of the deoxynucleoside triphosphate pools to regain sensitivity.

SUMMARY OF THE INVENTION

The subject invention has been directed at development of an anti-contamination chemistry for reactions following amplification reactions for nucleic acids that do not exhibit the drawbacks of the various processes described. In particular, anti-contamination chemistry for processes in which RNA is employed such as NASBA is desirable. Furthermore, the process according to the invention is based on partial degradation of amplified product whilst still enabling detection of the amplified product by oligonucleotide hybridisation. Degradation of nucleic acid can be accomplished by using specific DNases (DNase, I, restriction enzymes, endonucleases, exonucleases) and RNases (RNase A, RNase T1, RNase U, exonuclease) or using non-specific nucleases capable of simultaneous degradation of both DNA and RNA (S1 nuclease, DNaseI not RNase free etc.).

The subject invention is directed at a process for making the product of a nucleic acid amplification reaction, which amplification reaction employs one or more primer pairs, incapable of being a target for further amplification comprising: contacting the amplified product with an oligonucleotide capable of hybridizing to a stretch a nucleotides of the amplified product, said stretch being situated between the hybridisation sites of a pair of primers, under conditions which allow formation of a hybridisation complex between the oligonucleotide and the amplified product to occur, said oligonucleotide being modified in such a way that it protects the double stranded part of the hybridisation complex hybridized to the oligonucleotide from degradation, and subjecting the hybridisation complex to a degradative treatment under circumstances such that at least the part of the hybridisation complex capable of hybridizing to the primers is degraded.

DETAILED DESCRIPTION OF THE INVENTION

In the process according to the invention the detection oligonucleotide preferably comprises a 3' terminus that cannot be elongated with another nucleotide. The means by which this can be achieved is known to a person skilled in the art. Furthermore, in a suitable embodiment of the invention the step of partial degradation of the hybridisation complex can be executed by using a nuclease for which the complex of amplified product and detection oligonucleotide is insusceptible to degradation. An example of a detection oligonucleotide being insusceptible to degradation by nuclease is an oligonucleotide comprising 2'-O -methyl modification of a number of nucleotides sufficient to prevent degradation by nuclease, preferably comprising only nucleotides modified in said manner. In the case of a NASBA amplification reaction both DNA and RNA have to be degraded simultaneously in order for the method to be successful as both DNA and RNA are amplified. Therefore, in such a case the process according to the invention can be carried out with a nuclease or a mixture of nucleases directed at degrading both DNA and RNA. It is also possible to carry out the degradation using specific DNase such as DNase I, a restriction enzyme, an endonuclease or an exonuclease for solely degrading DNA. Specifically for degrading RNA, specific RNase such as RNase T can be used, as can RNase U, RNase A or an exonuclease. It is also possible to carry out the degradation using non- specific nuclease capable of simultaneous degradation of both DNA and RNA. In another embodiment the degradation step of the process can be carried out chemically rather than enzymstically with nuclease.

In summary, in particular embodiments of the invention the combined use of nucleases and nuclease resistant probes (2'-O-Me-oligonucleotides) to prevent contamination of amplification reactions, in particular amplification reactions using RNA such as NASBA amplification reactions with previously generated amplification products whilst still enabling detection of amplification products e.g. by hybridisation analysis is unique. The described anticontamination chemistries or methods known to date will not work in RNA amplification reactions such as NASBA. The only exception to this being the post-amplification sterilisation method of amplification product using isopsoralens which could in theory be used. However, to date no suitable isopsoralens have been found that in practice are compatible with NASBA amplifications. The subject method can be used for preventing contamination of all types of amplification reactions but in particular solves the problem of contamination of RNA amplification reactions such as NASBA reactions. When the process is in particular directed at eliminating carry-over due to aerosol droplets the process should preferably be used such that there is a non-detectable amount of amplifiable amplification product present in an aerosol droplet of that final reaction mixture, i.e. there should be no more than $10^5$ molecules of amplifiable product per μl, preferably no more than $10^4$ molecules of amplifiable product per μl. This can be arranged by use of sufficient amount of nuclease. A person skilled in the art will be able to determine this on the basis of the activity of the nuclease. As nuclease activity varies per batch so no concrete amounts can be given. This will have to be determined on an ad hoc basis, which is well known to a person skilled in the art.

In the process according to the invention the oligonucleotide can be used for detection purposes but it can also serve for immobilisation. If the oligonucleotide is to serve for detection purposes it can be provided with a detectable marker, such as an enzyme (HRP, AP) a fluorescent group, an electrochemiluminescent label, a dye or a radioactive isotope. Any generally used detectable markers known for detection of hybridised nucleic acid can be used in the process according to the invention and will be apparent to a person skilled in the art. The process according to the invention can also be carried out by adding a second oligonucleotide prior to the degradation, said second oligonucleotide being sufficiently homologous with a stretch of nucleotides of the amplified product for hybridisation with the amplified nucleic acid to occuP. Such a second oligonucleotide will be used provided with a detectable marker when the first oligonucleotide is used for immobilisation purposes and vice versa. The second oligonucleotide can be added simultaneously with the first oligonucleotide. The stretch of nucleotides for hybridisation of the second oligonucleotide being situated between the hybridisation sites of two primers used for amplification and being within four nucleotides of the last nucleotide of the stretch of the amplified product which hybridizes to the first oligonucleotide. Preferably, the oligonucleotides are selected such that there exists as small a gap as possible between the two oligonucleotides with most preference for adjacency and circumstances are created such that hybridisation occurs resulting in a hybridisation complex of both oligonucleotides with amplified product. It is also possible to add the two oligonucleotides after each other also with an intermediate rinsing step. The oligonucleotide can be immobilized via the 5' or 3' terminus in a manner known per se and subsequently be detected in a manner known per se. In the case of the second oligonucleotide being added the second nucleotide can be provided at the 5' or 3' terminus with a detectable marker or vice versa the first nucleotide can be pPovided with a detectable marker and the second can immobilize the complex. It is also possible in an embodiment of the invention that one of the oligonucleotides exhibits tailing at the side proximal to and preferably adjacent to the last nucleotide of the stretch of the amplified product which hybridizes with the other oligonucleotide. In a preferred embodiment it is also possible for both the oligonucleotides to exhibit tailing at the proximal sides, preferably at the nucleotide sites adjacent to the last nucleotide of the stretch of the amplified product which hybridizes with the other oligonucleotide. It is then preferable that the tails are complementary over a length of at least 2 nucleotides, preferably over a length of more than 4 nucleotides as this appears to stabilize the resulting complex.

An oligonucleotide to be used in the invention preferably hybridizes to the amplified product over a length of at least 10 nucleotides, preferably over a length of 11–30 nucleotides to ensuPe good hybridisation and stability under the conditions of an amplification reaction. The method can also be carried out using nucleic acid, specific antibody for detection or immobilisation, said antibody recognizing nucleic acid between primer pairs.

The hybridisation and degradation steps can be carried out successfully at a temperature between 30°–80° C., preferably between 40°–70° C., with more preference for a temperature between 40°–64° C. This temperature range means that the method is extremely suitable for use in NASBA amplification reactions.

In order to minimize the risk of carry-over contamination the process according to the invention is preferably carried out in such a manner that the container of the amplified product is opened as few times as possible, prior to the degradation of amplified product and preferably the container is opened only once, with more preference for not being opened at all. In the process according to the invention addition of reactants occurs in such a manner that hybridisation takes place prior to degradation in the container. The invention is not only directed at the process described but also at an assay for diagnosing the presence of a specific nucleic acid sequence in a sample comprising a) isolating nucleic acid from a sample in a manner known per se
b) amplifying a part of the nucleic acid comprising at least a part of the sequence to be detected using a primer pair or multiple primer pairs where each pair flanks at least a part of the sequence to be detected in a manner known per se
c) carrying out the method according to the invention as disclosed above on the amplification mixture resulting from b) and
d) detecting the detectable marker of the oligonucleotide amplification product resulting from step c) in a manner known per se. Such a method should be able to be carried out in a routine manner in a clinical laboratory thereby enabling diagnostic tests to be carried out after amplification reaction without the concomitant risk of carry-over infection with amplicon.

The invention is also directed at a kit for carrying out the anticontamination method of the invention or the assay as disclosed, said kit comprising in particular 1) a primer pair or multiple primer pairs for amplification of the desired sequence
2) a set of one or two oligonucleotides per primer pair capable of hybridizing to the amplified sequence at a location between a primer pair with the proviso when two oligonucleotides are present that their sequences are such that they will hybridize with the amplified sequence within 4 nucleotides of each other, preferably adjacent to each other and that preferably each oligonucleotide is complementary to the amplified product over a length of at least 10 nucleotides with a preference for 11–30 nucleotides.

In a suitable embodiment a kit according to the invention comprises an oligonucleotide with a modification in the form of 2'-O-methyl on a sufficient number of nucleotides to render the hybridized part of the complex of amplified product and oligonucleotide undegradable by nuclease, said modiifcation preferably being present on all nucleotides of the oligonucleotide. Furthermore, a kit especially suited for carrying out the invention will preferably further comprise the compound or compounds required for partical degradation of the nucleic acid, e.g. the nuclease in sufficient amount for degradation of the amplified nucleic acid. The specific nuclease or nucleases to be included will depend on the amplification reaction to be carried out, e.g. DNase and RNase for NASBA or DNase for PCR. With a view to minimizing the number of times the vessel comprising amplified product is opened the kit according to the invention should comprise the compound or compounds required for partial degradation of the nucleic acid, e.g. the nuclease in a container in which the process is to be carried out in such a manner that the compound or compounds required for partial degradation of the nucleic acid, e.g. the nuclease can only contact the reaction mixture after hybridisation of the oligonucleotide or oligonucleotides to the amplified product has occurred. A container suitable for carrying out the process according to the invention or for use in a kit according to the invention falls within the scope of the invention. Such a container comprises the compound or compounds required for partial degradation of the nucleic acid, e.g. the nuclease in a separate compartment in the container, said separate compartment being degradable enabling contact of the compound or compounds required for partial degradation of the nucleic acid, e.g. the nuclease with the rest of the container after degradation of the separate compartment. The wall of the separate compartment can, for example, comprise a thermodegradable substance, degradable at a temperature below the inactivation temperature of the compound or compounds required for partial degradation of the nucleic acid, e.g. the nuclease and below the melting out temperature of the hybridisation complex. Examples of such a thermodegradable substance are wax or agarose. Any other sort of equivalent delayed release system of the compound or compounds required for partial degradation of the nucleic acid, e.g. the nuclease will be obvious to a person skilled in the art. The idea being that the container in which the reactio or amplification is carried out is opened as little as possible in order to reduce the risk of carry-over. The invention is further illustrated in the following Examples, and should not be considered as being only restricted thereto.

EXAMPLE 1

NASBA reactions were performed according to Kievits et al. (1990) and van Gemen et al. (1993) with minor modifications. To 2 µl HIV-1 target nucleic acid (RNA) 21 µl reaction mixture was added (final concentrations: 40 mM Tris, pH 8.5, 42 mM KCl, 12 mM $MgCl_2$, 5 mM DTT, 15% v/v DMSO, 1 mM each dNTP, 2 mM each NTP, 0.2 µm primer 1 and 0.2 µm primer 2) and incubated at 65° C. for 5 minutes. After cooling down to 41° C. the amplification was started by addition of 2 µl enzyme mix (final concentrations: 0.1 µl BSA, 0.1 U RNase H, 8 U AMV-reverse transcriptase and 40 U $T_7$ RNA polymerase). Reactions were incubated for 75 minutes at 41° C. in a total volume of 25 µl. Nuclease treatment of amplified NASBA products was performed by mixing 5 µl NASBA reaction mixture, 5 µl 1× NRG buffer (40 mM Tris, pH=8,5, 42 mM KCl, 12 mM $MgCl_2$, 5 mM DTT, 1 mM each dNTP, 1 mM each NTP), 1 µl 100 mM $MgCl_2$, and RNase A and DNase I at concentrations stated in Table 1. The final volume was 15 µl and incubation was at 41° C. for 30 minutes. For each nuclease incubation serial dilutions wer made and 2 µl of appropriate dilutions were used as input for NASBA re-amplification reactions. These reamplifications were performed without the 65° C. incubation.

The results are summarized in Table 1. All tested combination of RNase A (50 mg) and DNase I (100–500 U) prevent re-amplification of NASBA amplified products. Input volumes of original NASBA reactions in re-amplification NASBA reactions larger than $2\times10^3$ µl were all positive. However, such relative high volumes are too large to form an aerosol so the potential of these large volumes to contaminate a NASBA is low.

TABLE 1

Re-amplification of NASBA products without 65° C. incubation after nuclease treatment with RNase A and DNase I

| | | Input volume of original NASBA reaction in re-amplification NASBA (µl) | | |
|---|---|---|---|---|
| RNase | DNase I | $2 \times 10^{-3}$ | $2 \times 10^{-6}$ | $2 \times 10^{-9}$ |
| 50 ng | 100 U (Pharmacia) | ± | + | − |
| 50 ng | 250 U (Pharmacia) | ± | − | + |
| 50 ng | 500 U (Pharmacia) | ± | − | − |
| 50 ng | 100 U (Gibco BRL) | ± | − | − |
| 50 ng | 250 U (Gibco BRL) | ± | − | − |
| 50 ng | 500 U (Gibco BRL) | ± | − | − |
| 50 ng | 100 U (Boehringer) | ± | − | − |
| 50 ng | 250 U (Boehringer) | ± | − | − |
| 50 ng | 500 U (Boehringer) | − | − | − |
| — | — | + | + | + |

DNase I of 3 suppliers was tested.

EXAMPLE 2

NASBA amplifications and re-amplifications are identical to Example 1, with the difference that re-amplifications are performed with 65° C. incubation. The results are summarized in Table 2.

TABLE 2

Re-amplification of NASBA products with 65° C. incubation after nuclease treatment with RNase A and DNase I.

| RNase A | DNase I | Input volume of original NASBA in re-amplification NASBA (µl) | | |
|---|---|---|---|---|
| | | $2 \times 10^{-3}$ | $2 \times 10^{-4}$ | $2 \times 10^{-5}$ |
| 50 ng | 500 U | + | + | − |
| 50 ng | 700 U | + | + | − |
| 50 ng | 1000 U | + | − | − |
| 100 ng | 500 U | + | + | − |
| 100 ng | 700 U | + | + | − |
| 100 ng | 1000 U | + | ± | − |
| — | — | + | + | + |

In this example re-amplifications are also inhibited by nuclease treatment of NASBA amplified products, albeit to a lesser extent than was the case in Example 1. The inhibition of re-amplification of volumes of $2 \times 10^{-3}$ and $2 \times 10^{-4}$ µl is caused by negative effect of the nucleases on the NASBA reaction although some target nucleic acid may be present. The 65° C. incubation, however, kills the nuclease activity, enabling re-amplification of nucleic acid that is present. In preventing re-amplification with the 65° C. incubation DNase I concentration of 1000 Units in combination with RNase A concentration of 50 or 100 ng seems to work best.

EXAMPLE 3

NASBA amplification, re-amplification and nuclease treatment are the same as described in Example 1. In this Example a comparison was made between re-amplifications with and without the 65° C. incubation. The results are summarized in Table 3.

TABLE 3

Re-amplification of NASBA amplified products with and without 65° C. incubation after treatment with DNase I and RNase A.

| DNase I | RNase A | 65° C. incubation | Input volume of original NASBA reaction in re-ampl. NASBA (µl) | | |
|---|---|---|---|---|---|
| | | | $2 \times 10^{-3}$ | $2 \times 10^{-6}$ | $2 \times 10^{-9}$ |
| 500 U | 50 ng | yes | + | − | − |
| 500 u | 50 ng | no | − | − | − |
| — | —. | yes | + | + | + |

In the direct comparison of re-amplifications with and without the 65° C. incubations it appears that relatively high input volumes (i.e. $2 \times 10^{-3}$ µl) contain enough nuclease to inhibit the NASBA re-amplification reaction. The 65° C. incubation kills the nuclease activity and can thus enable re-amplification of nucleic present. In practice the carry-over volumes, when normal precautions are taken should be sufficiently low to avoid inhibition of the NASBA re-amplification reaction, so that the step of 65° C. incubation or any other step of inactivation should not be necessary. As a precautionary measure however, an inactivation step of the compound responsible for partial degradation of nucleic acid prior to re-amplicication can be carried out. This is valid not only for NASBA but all other types of amplification reactions.

EXAMPLE 4

NASBA amplifications, re-amplifications and nuclease treatment are performed as in Example 1. to check whether the inhibiting effect of re-amplifications without 65° C. when relatively high volumes are used (i.e. $2 \times 10^{-3}$ µl) is caused by nuclease activity in the input volume the following experiment was performed. NASBA amplifications were nuclease treated with 500 units DNase I and 50 ng RNase A and $2 \times 10^{-3}$ µl was added to an independent NASBA amplification with primers not capable of re-amplification, but specific for another target RNA sequence which were added to the amplification at concentrations stated in Table 4.

TABLE 4

NASBA amplification of an independent RNA target sequence after addition of $2 \times 10^{-3}$ µl of a DNase I/RNase A treated NASBA reaction

| Addition of DNase I/RNase A treated NASBA reaction | 65° C. incubation | Input RNA target sequence (molecules) | | | |
|---|---|---|---|---|---|
| | | $10^1$ | $10^2$ | $10^3$ | $10^4$ |
| None | yes | + | + | + | + |
| $2 \times 10^{-3}$ µl | yes | + | + | + | + |
| $2 \times 10^{-3}$ µl | no | − | − | − | − |

These results again demonstrate the presence of inhibiting nucleases in relatively high volumes in nuclease treated NASBA reactions. The nuclease activity can be killed by a 65° C. incubation of 5 minutes.

From Examples 1 to 4 it can be concluded that nuclease treatment in a method according to the invention is successful in preventing re-amplification of NASBA amplified products at concentrations of 1000 units DNase I and 50 ng RNase A. This approach is valid in re-amplifications performed with and without 65° C. incubation, albeit that at relatively high input ($2 \times 10^{-3}$ µl) re-amplification is inhibited, more efficiently when there is no 65° C. incubation due to presence of residual nucleases in the sample. Re-amplifications of nuclease treated NASBA amplified products with 65° C. incubation can be succesfully inhibited at a volume of $2 \times 10^{-4}$ µl amplified product or smaller (see Example 2).

EXAMPLE 5

NASBA amplifications and nuclease treatments are as described in Example 1. Following the nuclease treatment, or coinciding with the nuclease treatment the NASBA amplified product should be detected. Detection of the NASBA amplified product should be sequence specific, i.e. using one or more specific oligonucleotide probes. The following experiment was performed, after NASBA amplification the amplified products (1 µl) were hybridized with an oligonucleotide ($10^{12}$ molecules) in 1×NRG buffer for 30 minutes at 45° C. Hybridisations were done with single standard oligonucleotides, single 2'-O-methyl oligonucleotides, two adjacent standard oligonucleotides and two adjacent 2'-O-methyl oligonucleotides. The hybridisations were followed by RNase A (50 mg) and DNase I (500 units) treatment (see example 1). The nuclease treated hybdridisation examples were analysed on 20% acrylamide gel stained with ethidium bromide. The results are summarized in Table 5.

TABLE 5

Detection of NASBA amplified products after oligonucleotide hybridization and DNase I/NRase A treatment

| Oligonucleotide | | | | Signal on 20% acryl gel | |
|---|---|---|---|---|---|
| number | type | RNase | DNase I | 1 oligo + RNA | 2 oligo's + RNA |
| 1 | standard | — | — | + | |
| 1 | standard | 50 ng | 500 U | − | |
| 1 | 2'-O—Me | — | — | + | |
| 1 | 2'-O—Me | 50 ng | 500 U | + | |
| 2 | standard | — | — | | + |
| 2 | standard | 50 ng | 500 U | | − |
| 2 | 2'-O—Me | — | — | | + |
| 2 | 2'-O—Me | 50 ng | 500 U | | + |

These results indicate that the 2'-O-methyl oligonucleotides are resistant to nuclease treatment, and more importantly that the hybridisation complex between 2'-O-methyl oligonucleotides and amplified NASBA product (RNA) is resistant to nuclease treatment. The hybridisation complex between two adjacent 2'-O-methyl oligonucleotides and NASBA amplified product (RNA) is also resistant against cutting of the NASBA amplified product (RNA) opposite the "nick" between the two 2'-O-methyl oligonucleotides. These results enable the development of a sandwich hybridisation format resistant to nuclease treatment.

EXAMPLE 6

NASBA amplification and nuclease treatment are the same as described in Example 1. The NASBA amplified products were subject to hybridisation with 2'-O-methyl oligonucleotides using a sandwich format with magnetic beads, a biotinylated capture probe and a HRP-labelled detection probe. For this hybridisation both a one-step and a two-step protocol were used.

In the one-step method 5 µl NASBA amplified product was added to 55 µl hybridisation mixture (5×SSPE, 0,1% SDS, 0,1% milk powder, 10 µg/ml salmon sperm DNA, 3×10⁶ streptavadin coated magnetic beads, 15 p mol biotinylated 2'-O-Me capture probe, 1×10³ molecules HRP labelled 2'-O-Me detection probe) and incubated for 30 minutes art 45° C. The beads were washed twice with 2×SSC, 0.1% BSA nd resuspended in 1×NRG buffer plus 10 mM MgCl₂. DNase I and RNase A treatment were as in example 1. Subsequently the beads were washed twice with 1×TBS and the HRP labelled 2'-O-Me detection probe retained on the beads was detected by addition of a TMB/peroxide substrate (100 µl). The coloring reaction was stopped by addition of 50 µl 250 mM oxalic acid and the optical density read at 450 nm.

In the two-step protocol the NASBA reaction mixture 65 µl) was added to the same hybridisation mixture (5 µl) without the 2'-O-Me HRP labelled detection probe. Following a 30 minute 45° C. incubation the beads were washed twice with 2×SSC, 0.1% BSA and resuspended in 50 µl hybridisation mixture (5×SSPE, 0.1% SDS, 0.1% milk powder, 10 µl/ml salmon sperm DNA) and 1×10³ HRR labelled 2'-O-Me detection probe was added. Incubation was for 30 minutes at 45° C. Subsequently the beads were washed twice with 2×SSC, 0.1% BSA. DNase I and RNase A treatment were as in Example 1. The beads were washed twice with 2×TBS and the HRP labelled 2'-O-Me detection probe retained on the beads was detected by addition of a TMB/peroxide substrate (100 µl). The coloring reaction was stopped by addition of 50 µl 250 mM oxalic acid and the optical density read at 450 nM. The results are summarized in Table 6.

TABLE 6 detection of NASBA amplified products using 2'-O—Me capture and detection oligonucleotides in a sandwich hybridisation on beads.

| NASBA product | Protocol | RNase A | DNase I | OD 450 |
|---|---|---|---|---|
| — | one step | — | — | 0.05 |
| 5 µl | " | — | — | 1.70 |
| 5 µl | " | 50 ng | — | 1.40 |
| 5 µl | " | — | 500 U | 0.80 |
| 5 µl | " | 50 ng | 500 U | 0.70 |
| — | two-step | — | — | 0.05 |
| 5 µl | " | — | — | 1.20 |
| 5 µl | " | 50 ng | — | 0.80 |
| 5 µl | " | — | 500 U | 1.00 |
| 5 µl | " | 50 ng | 500 U | 0.80 |

In conclusion the RNase A/DNase I treatment has no effect on the detection of NASBA amplified products in the sandwich hybridisation assay using 2'-O-Me for oligonucleotides capture and detection.

We claim:

1. A process for making the product of a nucleic acid amplification reaction, which amplification reaction employs one of more primer pairs, incapable of being a target for further amplification comprising:

contacting an amplified product with an oligonucleotide capable of hybridizing to a stretch of nucleotides of the amplified product, said stretch being situated between the hybridization sites of a pair of primers, under conditions which allow formation of a hybridization complex between the oligonucleotide and the amplified product to occur, said oligonucleotide being modified in such a way that it protects the portion of the hybridization complex where said stretch is located from degradation; and subjecting the hybridization complex to a degradative treatment under circumstances such that at least the part of the hybridization complex capable of hybridizing to the primers is degraded.

2. A process according to claim 1 wherein the oligonucleotide comprises a 3' terminus that cannot be elongated with another nucleotide.

3. A process according to claim 1, wherein the degradation is carzied out using a nuuleaee for which the portion of the hybridization complex where said stretch is located is insusceptible.

4. A process according to claim 1, wherein the oligonucleotide is insusceptible to degradation by nuclease due to the presence of 2'-O-methyl modifications on a portion of the nucleotides of the oligonucleotide.

5. A process according to claim 1 wherein the degradation is carried out with a mixture of nucleases.

6. A process according to claim 1, wherein the degradation is carried out using at least one DNAse selected from the group consisting of DNAse I, a restriction enzyme, an endonuclease and an exonuclease.

7. A process according to claim 1, wherein the degradation is carried out using at least one RNAse selected from the group consisting of RNAse T, RNAse U, RNAse A and an exonuclease.

8. A process according to claim 1, wherein the degradation is carried out using a nonspecific nuclease capable of simultaneous degradation of both DNA and RNA.

9. A process according to claim 1, wherein the amount of nuclease used is sufficient to ensure the presence of a non-detectable amount of amplifiable amplification product in an aerosol droplet of the final reaction mixture.

10. A process according to claim 1, wherein the amplification reaction is carried out by amplifying RNA.

11. A process according to claim 1, wherein the amplification reaction is the NASBA amplification reaction.

12. A process according to claim 1, wherein the oligonuclectide comprises a detectable marker selected from the group consisting of an enzyme, a fluorescent group, an electrochemilumineecent label, a dye and a radioactive isotope.

13. A process according to claim 1, wherein prior to the degradation an additional oligonucleotide is contacted with the amlified product, said additional oligonucleotide being sufficiently homologous with a stretch of nucleotides of the amplified product for hybridization with the amplified nucleic acid to occur, said stretch of nucleotides being situated between the hybridization sites of two primers used for amplification and being within 4 nucleotides of the last nucleotide of the stretch of the amplified product which hybridizes to the oligonucleotide set forth in claim 1, under circumstances such that hybridization occurs resulting in a hybridization complex of both oligonucleotides with amplified product.

14. A process according to claim 13, wherein one of the oligonuclectides is immobilized via the 5' or 3' terminus and the other oligonucleotide is provided at the 5' or 3' terminus with a detectable marker.

15. A process according to claim 14, wherein one of the oligonucleotides exhibits tailing at the nucleotide site adjacent to the last nucleotide of the stretch of the amplified product which hybridises with the other oligonucleotide.

16. A process according to claim 14, wherein both the oligonucleotides exhibit tailing st the nucleotide site adjacent to the last nucleotide of the stretch of the amplified product which hybridises with the other oligonucleotide.

17. A process according to claim 16, wherein the tails are complementary over a length of at least 2 nucleotides.

18. A process according to claim 1, wherein the oligonucleotide hybridizes to the amplified product over a length of at least 10 nucleotides.

19. A process according to claim 1, wherein the hybridization and degradation steps are carried out at a temperature between 30°–80° C.

20. A process according to claim 1, wherein a container holding the amplified product is opened at most only once prior to the degradation of amplified product, and the addition of reactants occurs in such a manner that hybridization takes place prior to degradation.

21. An assay for diagnosing the presence of a specific nucleic acid sequence in a sample comprising:

a) isolating nucleic acid from a sample;

b) amplifying a part of the nucleic acid comprising at least a part of the sequence to be detected using two primers that flank at least part of the sequence to be detected;

c) carrying out the method according to claim 1 on the amplification mixture resulting from b); and d) detecting the detectable marker of the oligonucleotide-amplification product resulting from step c).

22. A process according to claim 5, wherein said 2'-O-methyl modifications are present on each of the nucleotides forming the oligonucleotide.

23. A process according to claim 9, wherein the amount of nuclease used is no more than $10^5$ molecules/μl.

24. A process according to claim 9, wherein the amount of nuclease used is no more than $10^4$ molecules/μl.

25. A process according to claim 13, wherein the oligonucleotides hybridize at adjacent sites on the amplified product.

26. A process according to claim 17, wherein the tails are complementary over a length of more than 4 nucleotides.

27. A process according to claim 18, wherein the oligonucleotide hybridizes to the amplified product over a stretch of 11–30 nucleotides.

28. A process according to claim 1, wherein the hybridization and degradation steps are carried out at a temperature between 40°–70° C.

29. A process according to claim 1, wherein the hybridization and degradation steps are carried out at a temperature between 40°–64° C.

* * * * *

UNITED STATES PATENT AND TRADEMARK OFFICE
CERTIFICATE OF CORRECTION

PATENT NO. : 5,679,553
DATED : October 21, 1997
INVENTOR(S) : Van Gemen et al.

It is certified that error appears in the above-identified patent and that said Letters Patent is hereby corrected as shown below:

On the title page, item [54], and Column 1, line 2:

change "AMPLICATION" to -- AMPLIFICATION --.

Column 12, line 27, by changing the first occurence of "of" to -- or --; and line 46, change "carzied" to -- caried --, and change "nuucleaee" to -- nuclease --.

Column 13, line 10, by changing "electrochemilumineecent" to -- electrochemiluminescent --; and line 14, change "amlified" to -- amplified --.

Column 14, line 17, by changing "detacting" to -- detecting --.

Signed and Sealed this

Third Day of March, 1998

Attest:

BRUCE LEHMAN

*Attesting Officer*   Commissioner of Patents and Trademarks